US008153751B2

(12) United States Patent
Heo et al.

(10) Patent No.: US 8,153,751 B2
(45) Date of Patent: Apr. 10, 2012

(54) MULTIFUNCTION URETHANE MONOMER, METHOD OF MANUFACTURING THE MONOMER AND PHOTOSENSITIVE RESIN COMPOSITION INCLUDING THE MONOMER

(75) Inventors: Yoon Hee Heo, Daejeon (KR); Min Young Lim, Gyeonggi-do (KR); Ho Chan Ji, Daejeon (KR); Sung-Hyun Kim, Daejeon (KR); Han Soo Kim, Daejeon (KR); Sun Hwa Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/867,626

(22) PCT Filed: Jun. 30, 2009

(86) PCT No.: PCT/KR2009/003541
§ 371 (c)(1),
(2), (4) Date: Aug. 13, 2010

(87) PCT Pub. No.: WO2010/041810
PCT Pub. Date: Apr. 15, 2010

(65) Prior Publication Data
US 2010/0331439 A1 Dec. 30, 2010

(30) Foreign Application Priority Data
Oct. 6, 2008 (KR) .................. 10-2008-0097630

(51) Int. Cl.
*C08G 18/06* (2006.01)
*C08G 18/04* (2006.01)
*C08F 2/52* (2006.01)

(52) U.S. Cl. ............... 528/73; 528/44; 528/48; 528/49; 528/59; 528/65; 528/75; 522/90; 522/96; 522/173; 522/174; 430/270.1; 430/280.1; 430/284.1; 430/286.1; 430/287.1

(58) Field of Classification Search .............. 528/79, 528/44, 48, 49, 59, 65, 73, 75; 522/90, 96, 522/173, 174, 150, 151, 152; 430/280.1, 430/270.1, 284.1, 286.1, 287.1
See application file for complete search history.

(56) References Cited

U.S. PATENT DOCUMENTS

| 4,918,150 A * | 4/1990 | Sakakibara et al. .......... 525/502 |
| 4,943,516 A * | 7/1990 | Kamayachi et al. ........ 430/280.1 |
| 5,008,351 A * | 4/1991 | Paar .............................. 525/528 |
| 5,538,821 A * | 7/1996 | Kakinuma et al. .............. 430/18 |
| 5,639,828 A * | 6/1997 | Briggs et al. .................. 525/208 |
| 5,756,600 A * | 5/1998 | Okumura et al. ............. 525/528 |
| 5,852,136 A * | 12/1998 | Green ........................... 525/456 |
| 5,948,514 A * | 9/1999 | Komori et al. ................. 428/209 |
| 6,716,892 B1 * | 4/2004 | Mori et al. ....................... 522/92 |
| 7,374,862 B2 * | 5/2008 | Tanaka et al. .............. 430/284.1 |
| 2007/0166642 A1 | 7/2007 | Inoue |
| 2007/0185297 A1 * | 8/2007 | Tanaka et al. ................... 528/10 |
| 2008/0096133 A1 * | 4/2008 | Kato et al. ................. 430/286.1 |
| 2008/0271912 A1 * | 11/2008 | Yoshida et al. ............... 174/250 |

FOREIGN PATENT DOCUMENTS

| EP | 0633503 | 1/1995 |
| JP | 06-295060 A | 10/1994 |
| JP | 2002-338652 A | 11/2002 |
| JP | 2006-011395 | 1/2006 |
| JP | 2006-11395 A | 1/2006 |
| JP | 2008-007694 A | 1/2008 |
| KR | 10-0299264 | 11/2001 |
| KR | 10-2006-124758 | 12/2006 |
| KR | 10-0720283 | 5/2007 |
| KR | 10-0725432 | 6/2007 |
| KR | 10-0725432 B1 | 6/2007 |
| WO | WO 00/52530 | 9/2000 |
| WO | WO 00/56798 A1 | 9/2000 |
| WO | WO 01/27182 A1 | 4/2001 |
| WO | WO 2004/079452 | 9/2004 |

* cited by examiner

*Primary Examiner* — Sanza McClendon
(74) *Attorney, Agent, or Firm* — McKenna Long & Aldridge LLP

(57) ABSTRACT

Disclosed is a multifunctional urethane monomer prepared by reacting (a) an epoxy compound having two or more epoxy groups, (b) a diol compound having an acidic group and (c) a compound having an ethylenically unsaturated group and an isocyanate group with one another. The photosensitive resin composition comprising the multifunctional urethane monomer has low viscosity, superior sensitivity, excellent chemical resistance and heat-resistance and high development margin.

10 Claims, No Drawings

MULTIFUNCTION URETHANE MONOMER, METHOD OF MANUFACTURING THE MONOMER AND PHOTOSENSITIVE RESIN COMPOSITION INCLUDING THE MONOMER

This application is a 35 U.S.C. §371 National Stage entry of International Application No. PCT/KR2009/003541, filed on Oct. 6, 2008, and claims priority to Korean Application No. 10-2008-0097630, filed on June 10, 2008, which both hereby incorporated by reference in their entireties.

TECHNICAL FIELD

The present invention relates to a multifunctional urethane monomer, a method for preparing the same and a photosensitive resin composition comprising the same. More specifically, the present invention relates to a multifunctional urethane monomer for a photo-polymerizable negative-type photosensitive resin composition with superior sensitivity, heat-resistance, chemical-resistance and development margin.

BACKGROUND ART

Photo-polymerizable, negative-type photosensitive resin compositions are used for color filter photoresists, overcoat photoresists, column spacers, photo-shielding insulating materials and the like. Such a composition generally comprises an alkaline soluble resin, a polymer having at least one ethylenically unsaturated bond, a polymerizable initiator and a solvent.

Such a photosensitive resin composition is used in such a manner that the composition is coated on a substrate to form a thin film, a predetermined portion of the thin film is exposed to irradiation using a photo-mask and the non-exposed region is developed, to form a pattern.

Applications of liquid crystal displays (LCDs) have been expanded from conventional notebook monitors to desktop monitors, LCD TVs and the like, thus inevitably causing an increase in concentration of pigment present in a color filter photoresist and fine-dispersion of the pigment in order to realize high-quality colors. In order to realize thinner films, a concentration of light-shielding material, such as carbon black or titanium black, in a resin black matrix composition gradually increases.

As the concentration of the pigment or light-shielding material in the photosensitive resin composition increases, a level of irradiation transferred to the bottom of patterned films is rapidly decreased. Conventional compositions cannot satisfy requirements such as heat-resistance and chemical-resistance of LCD panel makers who decrease the level of irradiation exposed in order to improve production efficiency. In an attempt to satisfy these requirements, the amount of the binder increases to improve heat-resistance and chemical-resistance and photosensitivity is improved using a high-sensitivity photo-polymerization initiator. However, there is a limitation in increasing the concentration of a binder in view of the content of the composition. Also, this increase causes an increase in viscosity of the composition and makes highly sensitive photo-polymerization initiator expensive.

Accordingly, there is a need for approaches to multifunctional monomers in order to improve chemical-resistance, heat-resistance and development margin.

DISCLOSURE

Technical Problem

Therefore, the present invention has been made in view of the above problems, and it is one object of the present invention to provide a multifunctional urethane monomer with superior development margin, heat-resistance and chemical-resistance.

It is another object of the present invention to provide a method for preparing a multifunctional urethane monomer with superior development margin, heat-resistance and chemical-resistance.

It is another object of the present invention to provide a photosensitive resin composition comprising a multifunctional urethane monomer with superior development margin, heat-resistance and chemical-resistance.

Technical Solution

In accordance with the present invention, the above and other objects can be accomplished by the provision of a multifunctional urethane monomer prepared by reacting (a) an epoxy compound having two or more epoxy groups, (b) a diol compound having an acidic group and (c) a compound having an ethylenically unsaturated group and an isocyanate group with one another.

The (a) epoxy compound having two or more epoxy groups may be selected from non-phenolic epoxy resins, bisphenol A epoxy resins, hydrogenated bisphenol A epoxy resins, bisphenol F epoxy resins, hydrogenated bisphenol F epoxy resins, bisphenol S epoxy resins, hydrogenated bisphenol S epoxy resins, novolac epoxy resins, aromatic epoxy resins, glycidyl ether resins, glycidyl amine resins and aliphatic, cycloaliphatic or aromatic epoxy compounds such as brominated derivatives thereof, and combinations thereof.

b) The diol compound having an acidic group may be represented by Formula I below:

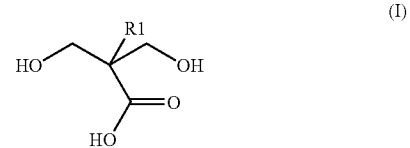

(wherein R1 is a methyl group or an ethyl group).

The c) compound may be represented by Formula II below:

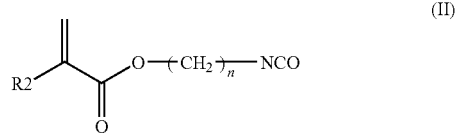

(wherein R2 is hydrogen or $C_1$-$C_5$ alkyl and n is an integer of 1 to 12).

The monomer may further comprise succinic anhydride, glutaric anhydride, methyl succinic anhydride, maleic anhydride, methyl maleic anhydride, phthalic anhydride, 1,2,3,6-tetrahydrophthalic anhydride, 3,4,5,6-tetrahydrophthalic anhydride, hexahydrophthalic anhydride, cis-5-norbornene-(endo, exo)-2,3-dicarboxylic acid anhydride or a combination thereof.

In accordance with another aspect, provided is a method for preparing a multifunctional urethane monomer comprising: mixing a) an epoxy compound having two or more epoxy groups with b) a diol compound having an acidic group, and heating the mixture in the presence of a solvent at 80 to 130° C. for 8 to 24 hours; and mixing the reaction mixture with c) a compound having an ethylene unsaturated group and an isocyanate group, and heating the mixture at 80 to 100° C. for 8 to 24 hours.

The solvent may be selected from methyl ethyl ketone, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, dipropylene glycol dimethyl ether, cyclohexanone, cyclopentanone, propylene glycol methyl ether acetate, propylene glycol ethyl ether acetate, 3-methoxybutyl acetate, methyl-3-methoxypropionate, ethyl 3-ethoxypropionate, ethyl cellosolve acetate, methyl cellosolve acetate, propyl cellosolve acetate, butyl cellosolve acetate, butyl acetate and a mixture thereof.

In accordance with another aspect, provided is a photosensitive resin composition comprising: a multifunctional urethane monomer prepared by reacting (a) an epoxy compound having two or more epoxy groups, (b) a diol compound having an acidic group and (c) a compound having an ethylene unsaturated group and an isocyanate group; an alkaline soluble resin; an ethylenically unsaturated compound; a photo-polymerization initiator; and a solvent.

With respect to 100 parts by weight of the composition, the multifunctional urethane monomer may be present in an amount of 1 to 20 parts by weight, the alkaline soluble resin may be present in an amount of 1 to 20 parts by weight, the ethylenically unsaturated compound may be present in an amount of 0.5 to 30 parts by weight, the photo-polymerization initiator may be present in an amount of 0.1 to 5 parts by weight and the solvent may be present in an amount of 25 to 95 parts by weight.

The resin composition may further comprise an alkaline soluble acrylate copolymer resin, a photo-accelerator, a coloring, a curing-accelerator, a thermal-polymerization inhibitor, a plasticizer, an adhesive accelerator, a filter, a surfactant or a combination thereof.

Advantageous Effect

The multifunctional urethane monomer of the present invention provides a photosensitive resin composition with low viscosity, superior sensitivity, excellent chemical resistance and heat-resistance, and high development margin.

BEST MODE

The present invention is directed to a multifunctional urethane monomer prepared by reacting (a) an epoxy compound having two or more epoxy groups, (b) a diol compound having an acidic group and (c) a compound having an ethylene unsaturated group and an isocyanate group with one another.

Hereinafter, the present invention will be described in detail.

a) The epoxy compound having two or more epoxy groups provides epoxy groups which react with the acidic group of b) the diol compound having at least one acidic group and improves heat-resistance and chemical-resistance of the multifunctional monomer according to the present invention.

Specifically, the epoxy resin is selected from the group consisting of non-phenolic epoxy resins, bisphenol A epoxy resins, hydrogenated bisphenol A epoxy resins, bisphenol F epoxy resins, hydrogenated bisphenol F epoxy resins, bisphenol S epoxy resins, hydrogenated bisphenol S epoxy resins, novolac epoxy resins, aromatic epoxy resins, glycidyl ether resins, glycidyl amine resins and aliphatic, cycloaliphatic or aromatic epoxy compounds such as brominated derivatives thereof, and combinations thereof. Preferred is a non-phenolic epoxy resin.

b) The diol compound having an acidic group may have a structure represented by Formula I below:

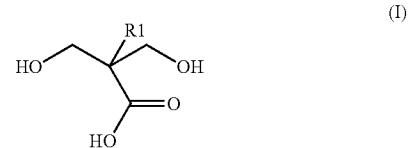

(I)

(wherein R1 is a methyl group or an ethyl group).

c) The compound having an ethylene unsaturated group and an isocyanate group may have a structure represented by Formula II below:

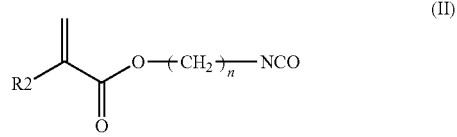

(II)

(wherein R2 is hydrogen or $C_1$-$C_5$ alkyl and n is an integer of 1 to 12).

In another aspect, the present invention is directed to a method for preparing a multifunctional monomer, comprising: (i) mixing a) an epoxy compound having two or more epoxy groups with b) a diol compound having an acidic group and heating the mixture in the presence of a solvent at 80 to 130° C. for 8 to 24 hours; and (ii) mixing the reaction mixture with c) the compound having an ethylene unsaturated group and an isocyanate group, and heating the mixture at 80 to 100° C. for 8 to 24 hours.

Preferably, a) the epoxy compound and b) the diol compound are mixed in a molar ratio of 1:m (m is a number of epoxy groups present in the epoxy compound). When the molar ratio of a) the epoxy compound to b) the diol compound is less than m (m is a number of epoxy groups present in the epoxy compound), the epoxy groups remain, thus disadvantageously causing storage stability.

The reaction concentration may be within the range of 10 to 100% by weight. When taking into consideration the fact that the reaction is a condensation reaction, as the reaction concentration increases, the reaction yield increases. However, in view of the risk of gelling which may occur upon reaction, load applied to an impeller of a reactor, and easy handling of the reaction solution after reaction, the reaction concentration is more preferably 30 to 80% by weight.

The number of alcohol groups produced by the reaction of the a) epoxy compound and the b) diol compound is 3*m (m is a number of epoxy groups in a molecule of the epoxy compound). In a subsequent step, the resulting reaction mixture reacts with c) the compound having an ethylene unsaturated group and an isocyanate group to produce a multifunctional monomer having photo-curable groups with urethane bonds.

The multifunctional monomer may further comprise acid monoanhydride, if necessary. The acid monoanhydride reacts with alcohol groups produced by the reaction of a) the epoxy compound with b) the diol compound, to form an acidic group.

Specifically, the acid monoanhydride may be selected from the group consisting of succinic anhydride, glutaric anhydride, methyl succinic anhydride, maleic anhydride, methyl maleic anhydride, phthalic anhydride, 1,2,3,6-tetrahydrophthalic anhydride, 3,4,5,6-tetrahydrophthalic anhydride, hexahydrophthalic anhydride and cis-5-norbornene-(endo, exo)-2,3-dicarboxylic anhydride and combinations thereof.

Preferably, the acid monoanhydride may be present in an amount of 5 to 50 mol % with respect to the multifunctional monomer. An acid value of the acid monoanhydride may be increased, depending on an amount of the acid monoanhydride added. When the amount of the acid monoanhydride exceeds 50 mol %, physical and chemical strengths of multifunctional monomers may be deteriorated.

When the acid monoanhydride is added, the reaction may be carried out at a reaction temperature of 70 to 110° C. for a reaction time of 4 to 24 hours. Under the temperature conditions, ethylene groups added by the condensation reaction may cause gelling through thermal polymerization. Thermal-polymerization inhibitors suitable for the polymerization reaction may be used under an atmosphere of oxygen. A representative example of thermal-polymerization inhibitors is 4-methoxyphenol (MEHQ) and 2,6-di-tibutyl-4-methyl phenol and the like.

Any solvent may be used without particular limitation so long as it includes no alcohol group and has a melting point not less than a reaction temperature.

Specifically, examples of solvents that can be used in the present invention include methyl ethyl ketone, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, dipropylene glycol dimethyl ether, cyclohexanone, cyclopentanone, propylene glycol methyl ether acetate, propylene glycol ethyl ether acetate, 3-methoxybutyl acetate, methyl-3-methoxypropionate, ethyl 3-ethoxypropionate, ethyl cellosolve acetate, methyl cellosolve acetate, propyl cellosolve acetate, butyl cellosolve acetate, butyl acetate and combinations thereof.

Catalysts that can be used in the present invention may be selected from catalysts for condensation reactions known in the art and examples thereof include alkaline catalysts such as alkyl ammonium, triphenylphosphine, triphenylantimony, dimethylaminopyridine and the like.

The photosensitive resin composition using the multifunctional urethane monomer prepared by the method exhibits improved sensitivity and adhesion and superior heat-resistance and chemical-resistance, as compared to conventional multifunctional monomers.

In addition, the present invention provides a photosensitive resin composition comprising the following ingredients:
1) a multifunctional urethane monomer prepared by reacting (a) an epoxy compound having two or more epoxy groups, (b) a diol compound having an acidic group and (c) a compound having an ethylene unsaturated group and an isocyanate group;
2) an alkaline soluble resin;
3) a polymeric compound having ethylenically unsaturated bonds;
4) a photopolymerization initiator; and
5) a solvent Of the ingredients of the photosensitive resin composition according to the present invention, the 1) multifunctional urethane monomer may be present in an amount of 1 to 20 parts by weight, with respect to the total parts by weight (100 parts by weight) of the photosensitive resin composition. When the content of the multifunctional urethane monomer is less than 1 part by weight, the strength of patterns is decreased. When the content of the monomer exceeds 20 parts by weight, viscosity of the composition thus prepared is excessively decreased, thus making it difficult to maintain uniformity of coated films.

Of the ingredients of the photosensitive resin composition, 2) the alkaline soluble resin may be present in an amount of 1 to 20 parts by weight, with respect to the total parts by weight (100 parts by weight) of the photosensitive resin composition. When the content of the multifunctional urethane monomer is less than 1 part by weight or exceeds 20 parts by weight, viscosity of the composition thus prepared is excessively decreased or increased, or maintenance of uniformity of films during coating is difficult.

The preparation of the alkaline soluble resin may be carried out in accordance with the following two steps:

In a first step, the monomers including functional acid groups are copolymerized with aromatic and aliphatic vinyl monomers suitable for copolymerization to prepare alkaline soluble linear copolymers. Preferably, the aromatic and aliphatic vinyl monomers may be selected from those that can improve film strength. Monomers that can improve film strength may be selected from compounds having an aromatic ring.

The reaction may be carried out using one method selected from various polymerizations such as radical polymerization, cationic polymerization, anionic polymerization and condensation polymerization. Most preferred is use of radical polymerization in view of ease and economic efficiency of preparation.

For example, the preparation is carried out by mixing monomers with a polymerization solvent, heating the mixture at a predetermined temperature and removing oxygen by nitrogen purging. In addition, preferably, a radical polymerization initiator and a chain transfer agent are added to the resulting mixture and the polymerization temperature is maintained, if necessary. The polymerization temperature and time of the method may be determined taking into consideration the half life depending on the temperature of polymerization initiator used.

For example, half life of 2,2'-azobisisobutyronitrile (AIBN) at 70° C. is 4.8 hours and polymerization time of AIBN is thus preferably 6 hours or longer. Generally, the polymerization temperature is within the range of 50° C. to 150° C. and the polymerization time is within the range of 30 minutes to 48 hours.

The radical polymerization initiator may be selected from those well-known in the art and specific examples thereof include 2,2'-azobisisobutyronitrile (AIBN), 2,2'-azobis-(2,4-dimethylvaleronitrile), 2,2'-azobis-(4-methoxy-2,4-dimethylvaleronitrile), benzoyl peroxide, lauroylperoxide, t-butylperoxypivalate and 1,1'-bis-(bis-t-butylperoxy)cyclohexane and the like.

The chain transfer agent controls a weight average molecular weight and examples thereof include n-hexylmercaptan, n-octylmercaptan, n-dodecylmercaptan, t-dodecylmercaptan, thioglycolate, 3-mercaptopropionic acid, a-methylstyrene dimer and the like. The chain transfer agent is not limited thereto and may be selected from those well-known in the art.

Examples of monomers having an acidic group that can be used for preparation of the linear copolymers include (meth) acrylic acid, crotonic acid, itaconic acid, maleic acid, fumaric acid, monomethyl maleic acid, isoprene sulfonic acid, styrenesulfonic acid, 5-norbornene-2-carboxylic acid and the like.

Examples of the aromatic and aliphatic vinyl monomers copolymerizable with the monomer having an acidic group include styrene, chlorostyrene, α-methyl styrene, vinyl toluene, methyl(meth)acrylate, ethyl(meth)acrylate, butyl(meth) acrylate, benzyl(meth)acrylate, dimethylaminoethyl(meth) acrylate, isobutyl(meth)acrylate, t-butyl(meth)acrylate, cyclohexyl(meth)acrylate, isobornyl(meth)acrylate, dicyclofentanyl(meth)acrylate, 2-phenoxyethyl(meth)acrylate, tetrahydrofurfuryl(meth)acrylate, hydroxyethyl(meth)acrylate, 2-hydroxypropyl(meth)acrylate, 2-hydroxy-3-chloropropyl(meth)acrylate, 4-hydroxybutyl(meth)acrylate, acyloctyloxy-2-hydroxypropyl(meth)acrylate, ethylhexyl acrylate, 2-methoxyethyl(meth)acrylate, 3-methoxybutyl (meth)acrylate, ethoxydiethylene glycol(meth)acrylate, methoxytriethylene glycol(meth)acrylate, methoxytripropylene glycol(meth)acrylate, methoxypolyethylene glycol (meth)acrylate, phenoxydiethylene glycol(meth)acrylate, p-nonylphenoxypolyethylene glycol(meth)acrylate, p-nonylphenoxypolypropylene glycol(meth)acrylate, tetrafluoropropyl(meth)acrylate, 1,1,1,3,3,3-hexafluoroisopropyl (meth)acrylate, octafluoropentyl(meth)acrylate, heptadecafluorodecyl(meth)acrylate, tribromophenyl(meth) acrylate and the like.

In a second step, the resulting mixture reacts with an ethylenically unsaturated compound containing epoxy groups to incorporate photo-reactive groups into a solution obtained by copolymerizing monomers having a functional acid group with aliphatic or aromatic vinyl monomers, to prepare an alkaline soluble binder resin.

Examples of ethylenically unsaturated compounds include allyl glycidyl ether, glycidyl(meth)acrylate, 3,4-epoxycyclohexylmethyl(meth)acrylate, glycidyl 5-norbornene-2-carboxylate(endo, exo mixture), 5-norbornene-2-methyl-2-carboxylate(endo, exo mixture), 1,2-epoxy-5-hexene, 1,2-epoxy-9-decene and the like. The compound may be used alone or in combination thereof.

The reaction completion of the copolymer resin may be confirmed by measuring an acidic value of the resin having photo-reactive groups. The acidic value of copolymer resin thus prepared is calculated, the acidic value of copolymer resin is measured using a pH meter during the reaction, and the epoxy group disappears during the reaction, in the case where the measured value is close to the calculated value. The alkaline soluble binder resin serves as a matrix during formation of a photosensitive composition thin film and comprises a polymer imparting solubility to an alkaline aqueous developing solution.

Of ingredients of the photosensitive resin composition, non-limiting examples of 3) polymeric compounds having the ethylenically unsaturated bonds include compounds obtained by esterifying polyhydric alcohols such as ethylene glycol di(meth)acrylate, polyethylene glycol di(meth)acrylate containing 2 to 14 ethylene groups, trimethylolpropane di(meth)acrylate, trimethylolpropane tri(meth)acrylate, pentaerythritol tri(meth)acrylate, pentaerythritol tetra(meth) acrylate, 2-trisacryloyloxymethylethylphthalic acid, propylene glycol di(meth)acrylate having 2 to 14 propylene groups, dipentaerythritol penta(meth)acrylate, and dipentaerythritol hexa(meth)acrylate, with α,β-unsaturated carboxylic acid; compounds obtained by adding (meth)acrylic acid to compounds containing glycidyl groups such as trimethylolpropane triglycidyletheracrylic acid adducts, and bisphenol A diglycidyletheracrylic acid adducts; esters of the compound having hydroxyl groups or ethylenically unsaturated bonds, such as phthalic diester of β-hydroxyethyl(meth)acrylate and toluene diisocyanate adducts of β-hydroxyethyl(meth)acrylate, with polycarboxylic acid or their adducts with polyisocyanate; (meth)acrylic acid alkyl esters such as methyl(meth) acrylate, ethyl(meth)acrylate, butyl(meth)acrylate, 2-ethylhexyl(meth)acrylate and 9,9'-bis[4-(2-acryloyloxyethoxy)phenyl]fluorine, but are not limited thereto and may be selected from those known in the art. If necessary, silica dispersants may be used for these compounds, for example, Nanocryl XP series (0596, 1045, 21/1364, available from Hanse Chemie GmbH.) and Nanopox XP series (0516, 0525, available from Hanse Chemie Co., Ltd.).

3) The polymeric compound having ethylenically unsaturated bonds may be present in an amount of 0.5 to 30 parts by weight, based on 100 parts by weight of the photosensitive resin composition. When the amount of the polymeric compound is less than 0.5 parts by weight, pattern strength is deteriorated, and when the amount exceeds 30 parts by weight, adhesion of the resin layer is excessive and foreign materials are readily adhered thereto.

Of the ingredients of the photosensitive resin composition, non-limiting examples of 4) the photopolymerization initiator include triazine compounds such as 2,4-trichloromethyl-(4'-methoxyphenyl)-6-triazine, 2,4-trichloromethyl-(4'-methoxystyryl)-6-triazine, 2,4-trichloromethyl-(fipronil)-6-triazine, 2,4-trichloromethyl-(3',4'-dimethoxyphenyl)-6-triazine, 3-{4-[2,4-bis(trichloromethyl)-s-triazine-6-yl] phenylthio} propanoic acid; biimidazole compounds such as 2,2'-bis(2-chlorophenyl)-4,4',5,5'-tetraphenyl biimidazole, and 2,2'-bis(2,3-dichlorophenyl)-4,4',5,5'-tetraphenylbiimidazole; acetophenone-based compounds (Irgacure-369) such as 2-hydroxy-2-methyl-1-phenylpropan-1-one, 1-(4-isopropylphenyl)-2-hydroxy-2-methylpropan-1-one, 4-(2-hydroxyethoxy)-phenyl (2-hydroxy)propyl ketone, 1-hydroxycyclohexyl phenyl ketone, 2,2-dimethoxy-2-phenyl acetophenone, 2-methyl-(4-methylthiophenyl)-2-morpolyno-1-propan-1-one (Irgacure-907), 2-benzyl-2-dimethylamino-1-(4-morpolynophenyl)-butan-1-one; O-acyloxime compounds such as Irgacure OXE 01, Irgacure OXE 02 (Ciba Geigy); benzophenone compounds such as 4,4'-bis(dimethylamino)benzophenone, and 4,4'-bis(diethylamino)benzophenone; thioxanthone compounds such as 2,4-diethyl thioxanthone, 2-chloro thioxanthone, isopropyl thioxanthone, diisopropyl thioxanthone; phosphine oxide compounds such as 2,4,6-trimethylbenzoyl diphenylphosphine oxide, bis(2,6-dimethoxybenzoyl)-2,4,4-trimethylpentyl phosphine oxide, bis(2,6-dichlorobenzoyl) propyl phosphine oxide; coumarin compounds such as 3,3'-carbonylvinyl-7-(diethylamino)coumarin, 3-(2-benzothiazolyl)-7-(diethylamino)coumarin, 3-benzoyl-7-(diethylamino)coumarin, 3-benzoyl-7-methoxy-coumarin, and 10,10'-carbonylbis[1,1,7,7-tetramethyl-2,3,6,7-tetrahydro-1H,5H,11H—C1]-benzopyrano[6,7,8ij]-quinolizin- 11-one.

Preferably, 4) the photopolymerization initiator is present in an amount of 0.1 to 5 parts by weight with respect to 100 parts by weight of the photosensitive resin composition. When the amount of the photo-polymerization initiator is less than 0.1 parts by weight, curing participation level of the polymeric compound having ethylenically unsaturated bonds is deteriorated, and when the amount exceeds 5 parts by weight, radicals which do not participate in curing may cause contamination of the composition.

Of ingredients of the photosensitive resin composition of the present invention, non-limiting examples of 5) the solvent include methyl ethyl ketone, methyl cellosolve, ethyl cellosolve, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, 2-ethoxy propanol, 2-methoxy propanol, 3-methoxy butanol, cyclohexanone, cyclopentanone, propylene glycol methyl ether acetate, propylene glycol ethyl ether acetate, 3-methoxybutyl acetate, methyl 3-methoxypropionate, ethyl 3-ethoxypropionate, ethyl cellosolve acetate, methyl cellosolve acetate, butyl acetate, dipropylene glycol monomethyl ether and combinations thereof.

5) The solvent may be present in an amount of 25 to 95 parts by weight with respect to 100 parts by weight of the photosensitive resin composition.

If necessary, the photosensitive resin composition of the present invention may further comprise one or more additives such as alkaline soluble acrylate copolymer resins, photo-accelerators, colorings, curing-accelerators, thermal-polymerization inhibitors, plasticizers, adhesive accelerators, filters or surfactants.

The coloring may be at least one pigment, dye or a mixture thereof. Specifically, for example, black pigments may be metal oxide such as carbon black, graphite, black titanium, or the like. Examples of carbon black include SEAST 5HIISAF-HS, SEAST KH, SEAST 3HHAF-HS, SEAST NH, SEAST 3M, SEAST 300HAF-LS, SEAST 116HMMAF-HS, SEAST 116MAF, SEAST FMFEF-HS, SEAST SOFEF, SEAST VGPF, SEAST SVHSRF-HS and SEAST SSRF (Tokai Carbon Co., Ltd); diagram black II, diagram black N339, diagram black SH, diagram black H, diagram LH, diagram HA, diagram SF, diagram N550M, diagram M, diagram E, diagram G, diagram R, diagram N760M, diagram LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30 ЗOIL31B (Mitsubishi Chemical Co., Ltd.); PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100, and LAMP BLACK-101(Degussa Co., Ltd.); RAVEN-1100ULTRA, RAVEN-108OULTRA, RAVEN-106OULTRA, RAVEN-1040, RAVEN-1035, RAVEN-1020, RAVEN-1000, RAVEN-890H, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, RAVEN-1170 (Colombia carbon co., Ltd.) or combinations thereof.

In addition, examples of colorings for providing colors include CARMINE 6B (C.I.12490), PHTHALOCYANINE GREEN(C.I. 74260), PHTHALOCYANINE BLUE (C.I. 74160), PERYLENE BLACK (BASF K0084. K0086), CYANINE BLACK, LIONOL YELLOW (C.I.21090), LIONOL YELLOW GRO (C.I. 21090), benzidine yellow 4T-564D, VICTORIA PURE BLUE (C.I.42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264, 272; C.I. PIGMENT GREEN 7, 36; C.I. PIGMENT BLUE 15:1, 15:3, 15:4, 15:6, 16, 22, 28, 36, 60, 64; C.I. PIGMENT YELLOW 13, 14, 35, 53, 83, 93, 95, 110, 120, 138, 139, 150, 151, 154, 175, 180, 181, 185, 194, 213; C.I. PIGMENT VIOLET 15, 19, 23, 29, 32, 37, and in addition to, white pigments, fluorescence pigments and the like.

For example, the curing-accelerator may be selected from the group consisting of 2-mercaptobenzoimidazole, 2-mercaptobenzothiazole, 2-mercaptobenzooxazole, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), trimethylolethane tris(3-mercaptopropionate) and combinations thereof, but are not limited thereto, and may be selected from those known in the art.

For example, the thermal-polymerization inhibitor may be selected from the group consisting of p-anisole, hydroquinone, pyrocatechol, t-butyl catechol, N-nitrosophenylhydroxylamine ammonium, N-nitrosophenylhydroxylamine aluminum and phenothiazine and combinations thereof, but are not limited thereto, and may be selected from those known in the art.

Also, other plasticizers, adhesion accelerators, fillers and surfactants may be selected from all compounds that may be contained in conventional photosensitive resin compositions.

When, in addition to the alkaline soluble resin, the other additives are present, the coloring may be present in an amount of 0.5 to 20 parts by weight with respect to 100 parts by weight of the photosensitive resin composition and another additive may be present in an amount of 0.01 to 10 parts by weight.

In another embodiment, the present invention provides a cured material obtained from the photosensitive resin composition.

Examples of cured materials include, but are not limited to, red, green, blue color filter patterns or black matrix patterns and column spacers and the like.

The photosensitive resin composition may be used for roll coaters, curtain coaters, spin coaters, slot die coaters, various printing, settling and the like, and may be applied to the surface of supporters such as metals, papers, glass plastic substrates. In addition, the composition is applied on a supporter such as a film and the applied support is then transcribed onto another supporter. The application method is not particularly limited.

Examples of a light source to cure the photosensitive resin composition include mercury vapor arc, carbon arc and Xe arc to emit rays having wavelengths of 250 to 450 nm.

EXAMPLES

Now, the present invention will be described in more detail with reference to the following examples. These examples are provided only for illustrating the present invention and should not be construed as limiting the scope and spirit of the present invention.

Synthesis Example

Preparation of Multifunctional Monomer

Synthesis Example 1

791 g of 9,9-bisphenolfluorenediglycidylether, 459 g of dimethylolpropionic acid, 1.3 g of tetrabutylammonium bromide, and 3,750 g of propylene glycol monomethyl ether acetate (PGMEA) were stirred in a reactor (6 L) with a mechanical stirring machine. The reactor was heated to 115° C. while oxygen was passed into the reactor. After heating for 15 hours, the reaction was completed, 1,527 g of 2-isocyanatoethyl methacrylate and 1 g of monomethyl ether hydroquinone (MEHQ) were added to the resulting solution thus obtained and the resulting mixture was further reacted at 90° C. for 12 hours, to obtain a multifunctional urethane monomer 1 of Formula III. (Solid content: 44.37%, molecular weight: 2,040 (PDI: 1.049))

(III)

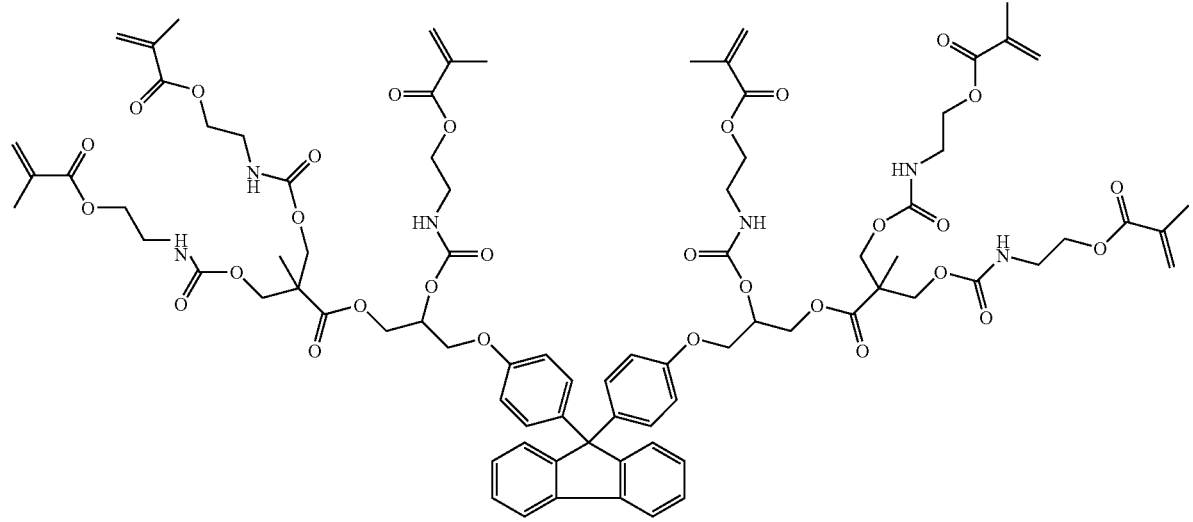

Synthesis Example 2

712 g of bixylenol epoxy resin YX4000HK (available from JER Co., Ltd.), 538 g of dimethylolpropionic acid, 1.3 g of tetrabutylammonium bromide, and 3,750 g of PGMEA were stirred in a reactor (6 L) with a mechanical stirring machine. The reactor was heated to 115° C. while oxygen was passed into the reactor. After heating for 15 hours, the reaction was completed, 1,792 g of 2-isocyanatoethyl methacrylate and 1 g of monomethyl ether hydroquinone (MEHQ) were added to the resulting solution thus obtained and the resulting mixture was further reacted at 90° C. for 12 hours, to obtain a multi-functional urethane monomer 2 of Formula IV. (Solid content: 45.50%, molecular weight: 1,540(PDI: 1.021))

Example

Preparation of Photosensitive Resin Composition

Example 1

35 g of 25% carbon black dispersion, 2.5 g of the multi-functional urethane monomer prepared in Synthesis Example 1, 12.4 g of an alkaline soluble resin (solid content: 3.5 g), 2.0 g of dipentaerythritol hexaacrylate as a polymeric compound, 1.5 g of photopolymerization initiator OXE-02, 0.5 g of 3-{4-[2,4-bis(trichloromethyl)-s-triazine-6-yl]phenylthio} propanic acid, 0.2 g of 4,4'-bis(diethylamino)benzophenone, and 44.5 g of PGMEA as an organic solvent were mixed with one another for 3 hours, to prepare a photosensitive resin composition.

Example 2

35 g of a 25% carbon black dispersion, 2.5 g of the multi-functional urethane monomer prepared in Synthesis Example 2, 10.7 g of an alkaline soluble resin (solid content 3.5 g), 2.0 g of dipentaerythritol hexaacrylate as a polymeric compound, 1.5 g of a photopolymerization initiator OXE-02, 0.5 g of 3-{4-[2,4-bis(trichloromethyl)-s-triazine-6-yl]phenylthio} propionic acid, 0.2 g of 4,4'-bis(diethylamino)benzophenone, 45.8 g of PGMEA as an organic solvent were mixed with one another for 3 hours to prepare a photosensitive resin composition.

(IV)

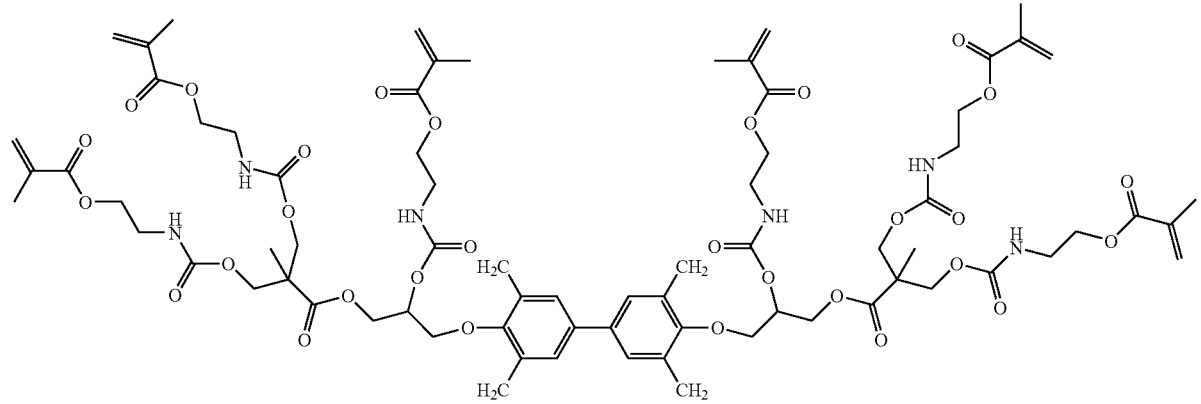

Comparative Example 1

A photosensitive resin composition was prepared in the same manner as in Example 1, except that 2.5 g of dipentaerythritol hexaacrylate was used instead of the multifunctional monomer of Synthesis Example 1.

Experimental Example

Evaluation of Sensitivity and Chemical-Resistance of Photosensitive Resin Composition The sensitivity and chemical-resistance of photosensitive resin composition were tested using the following method.

The photosensitive resin composition solutions prepared in Examples 1 and 2 and Comparative Example 1 were spin-coated on glass, and prebaked at about 100° C. for 2 minutes to form a film. The film thus formed was exposed to a high-pressure mercury lamp at an energy of 100 mJ/cm$^2$ using a photomask, and the resulting patterns were developed using a KOH alkaline aqueous solution (pH 11.3 to 11.7) at various times and washed with deionized water. The resulting patterns were post-baked at 220° C. for about 30 minutes.

The sensitivity of the photosensitive resin composition was determined from the minimum pixel size left after exposure using a Line & space mask and development.

In the case of the black matrix photoresist, the chemical-resistance of the photosensitive resin composition was determined from variation in thickness after immersing the composition in NMP(N-methylpyrrolidone) at 60° C. for 3 minutes.

Test results for the sensitivity and chemical-resistance are shown in Table 1 below.

In addition, in order to measure development margin, patterns were formed and developed for a predetermined period using a developing solution and the remaining pattern size was measured, and the results thus obtained are shown in Table 2 below:

TABLE 1

| Composition | Minimum pixel size (μm) | Thickness variation (%) |
|---|---|---|
| Ex. 1 | 5 | 1.2 |
| Ex. 2 | 5 | 1.5 |
| Comp. Ex. 1 | 15 | 2.9 |

As can be seen from Table 1, the photosensitive resin compositions of Examples 1 and 2 were applied to a black matrix photoresist, and as a result, the minimum pixel size left after development is 5 μm, which is less than the case of the composition of Comparative Example 1, thus exhibiting superior sensitivity. In addition, the resulting pixel after immersing in NMP for 3 minutes undergoes variation of 1.2 to 1.5%, which is higher than 2.9% of Comparative Example 1, thus exhibiting superior chemical-resistance.

TABLE 2

| Composition | Minimum pixel size (μm) | | |
|---|---|---|---|
| | 70 sec | 100 sec | 130 sec |
| Ex. 1 | 5 | 5 | 10 |
| Ex. 2 | 5 | 5 | 10 |
| Comp. Ex. 1 | 15 | 20 | 20 |

As can be seen from Table 2, the photosensitive resin compositions of Example 1 to 2 were applied to a black matrix photoresist and as a result, the compositions exhibited superior development margin and adhesion to a glass substrate as compared to Comparative Example 1. That is, recording of minimum pixel size as a function of developing time means that although the development time increases, even small size of patterns remain, and that development margin and adhesion to glass substrate are excellent. To allow micro patterns to remain even for long development time, the patterns should have superior adhesion to the substrate.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A multifunctional urethane monomer prepared by reacting (a) an epoxy compound having two or more epoxy groups, (b) a diol compound having an acidic group and (c) a compound having an ethylene unsaturated group and an isocyanate group with one another,
wherein the epoxy compound having two or more epoxy groups and the diol compound having an acidic group react at the molar ratio of 1:m, and m is a number greater than or equal to the number of epoxy groups present in the epoxy compound having two more epoxy groups.

2. The monomer according to claim 1, wherein the (a) epoxy compound having two or more epoxy groups is selected from non-phenolic epoxy resins, bisphenol A epoxy resins, hydrogenated bisphenol A epoxy resins, bisphenol F epoxy resins, hydrogenated bisphenol F epoxy resins, bisphenol S epoxy resins, hydrogenated bisphenol S epoxy resins, novolac epoxy resins, aromatic epoxy resins, glycidyl ether resins, glycidyl amine resins and aliphatic, cycloaliphatic or aromatic epoxy compounds such as brominated derivatives thereof, and combinations thereof.

3. The monomer according to claim 1, wherein b) the diol compound having an acidic group is represented by Formula I below:

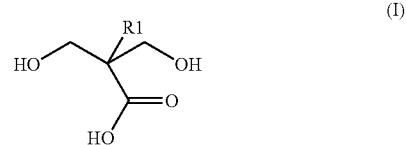

(I)

(wherein R1 is a methyl group or an ethyl group).

4. The monomer according to claim 1, wherein the c) compound is represented by Formula II below:

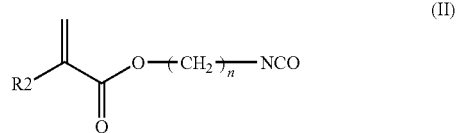

(II)

(wherein R2 is hydrogen or C$_1$-C$_5$ alkyl and n is an integer of 1 to 12).

5. The monomer according to claim 1, further comprising: succinic anhydride, glutaric anhydride, methyl succinic anhydride, maleic anhydride, methyl maleic anhydride, phthalic anhydride, 1,2,3,6-tetrahydrophthalic anhydride, 3,4,5,6-tetrahydrophthalic anhydride, hexahydrophthalic anhydride, cis-5-norbornene-(endo, exo)-2,3-dicarboxylic acid anhydride or a combination thereof.

6. A method for preparing a multifunctional urethane monomer comprising:

mixing a) an epoxy compound having two or more epoxy groups with b) a diol compound having an acidic group, and heating the mixture in the presence of a solvent at 80 to 130☐ for 8 to 24 hours; and mixing the reaction mixture with c) a compound having an ethylene unsaturated group and an isocyanate group, and heating the mixture at 80 to 100☐ for 8 to 24 hours, wherein the epoxy compound having two or more epoxy groups and the diol compound having an acidic group react at the molar ratio of 1:m, and m is a number greater than or equal to the number of epoxy groups present in the epoxy compound having two more epoxy groups.

7. The method according to claim 6, wherein the solvent is selected from methyl ethyl ketone, ethylene glycol dimethyl ether, ethylene glycol diethyl ether, propylene glycol dimethyl ether, propylene glycol diethyl ether, diethylene glycol dimethylether, diethylene glycol diethylether, diethylene glycol methyl ethyl ether, dipropylene glycol dimethylether, cyclohexanone, cyclopentanone, propylene glycol methyl ether acetate, propylene glycol ethyl ether acetate, 3-methoxybutyl acetate, methyl-3-methoxypropionate, ethyl 3-ethoxypropionate, ethyl cellosolve acetate, methyl cellosolve acetate, propyl cellosolve acetate, butyl cellosolve acetate, butyl acetate and a mixture thereof.

8. A photosensitive resin composition comprising:
a multifunctional urethane monomer prepared by reacting (a) an epoxy compound having two or more epoxy groups, (b) a diol compound having an acidic group and (c) a compound having an ethylene unsaturated group and an isocyanate group;
an alkaline soluble resin;
an ethylenically unsaturated compound;
a photopolymerization initiator; and
a solvent,
wherein the epoxy compound having two or more epoxy groups and the diol compound having an acidic group react at the molar ratio of 1:m, and m is a number greater than or equal to the number of epoxy groups present in the epoxy compound having two more epoxy groups.

9. The composition according to claim 8, wherein with respect to 100 parts by weight of the composition, the multifunctional urethane monomer is present in an amount of 1 to 20 parts by weight, the alkaline soluble resin is present in an amount of 1 to 20 parts by weight, the ethylenically unsaturated compound is present in an amount of 0.5 to 30 parts by weight, the photo-polymerization initiator is present in an amount of 0.1 to 5 parts by weight and the solvent is present in an amount of 25 to 95 parts by weight.

10. The composition according to claim 9, further comprising: an alkaline soluble acrylate copolymer resin, a photo-accelerator, a coloring, a curing-accelerator, a thermal-polymerization inhibitor, a plasticizer, an adhesive accelerator, a filter, a surfactant or a combination thereof.

* * * * *